(12) United States Patent
Schulze zur Wiesche et al.

(10) Patent No.: US 6,672,143 B2
(45) Date of Patent: Jan. 6, 2004

(54) PROCESS FOR DETERMINING THE DEGENERATION LEVEL OF KERATINIC FIBERS

(75) Inventors: Erik Schulze zur Wiesche, Hamburg (DE); Claudia Brockmann, Duesseldorf (DE); Detlef Hollenberg, Erkrath (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 0 days.

(21) Appl. No.: 10/165,062

(22) Filed: Jun. 7, 2002

(65) Prior Publication Data

US 2002/0178798 A1 Dec. 5, 2002

Related U.S. Application Data

(63) Continuation of application No. PCT/EP00/12265, filed on Dec. 6, 2000.

(30) Foreign Application Priority Data

Dec. 8, 1999 (DE) .......................... 199 59 213

(51) Int. Cl.$^7$ ............. G01N 29/00; G01N 3/30
(52) U.S. Cl. ............. 73/64.53; 73/866; 424/70.1; 132/202
(58) Field of Search ............. 73/64.53, 866; 424/70.1; 132/202

(56) References Cited

U.S. PATENT DOCUMENTS

| 4,865,774 A | 9/1989 | Fabry et al. ............. 252/554 |
| 4,931,218 A | 6/1990 | Schenker et al. ......... 252/551 |
| 5,131,417 A | * 7/1992 | Zaias et al. ............. 132/203 |
| 5,294,726 A | 3/1994 | Behler et al. ............ 554/98 |

FOREIGN PATENT DOCUMENTS

| DE | 37 23 354 | 1/1989 |
| DE | 37 25 030 | 2/1989 |
| DE | 39 26 344 | 2/1991 |
| DE | 44 32 854 | 3/1996 |
| EP | 0 148 994 | 7/1985 |
| FR | 2 473 284 | 7/1981 |
| JP | 63 163143 | 7/1988 |
| JP | 06 265544 | 9/1994 |
| JP | 08 101193 | 4/1996 |
| JP | 08 178920 | 7/1996 |

OTHER PUBLICATIONS

Database WPI, Section Ch, Week 199638, Derwent Publications Ltd., London, GB, AN 1996–374941, XP002164288 of JP 08 178920 (1996).

Patent Abstracts of Japan, vol. 012, No. 429 of JP 63 163143 (Nov. 1988).

Patent Abstracts of Japan, vol. 1996, No. 08 of JP 08 101193 (Aug. 1996).

Patent Abstracts of Japan, vol. 018, No. 670 of JP 06 265544 (Sep. 1994).

\* cited by examiner

Primary Examiner—Yogendra N. Gupta
Assistant Examiner—Eisa B Elhilo
(74) Attorney, Agent, or Firm—Stephen D. Harper; Gregroy M. Hill

(57) ABSTRACT

A process is provided for determining the degree of damage to keratinous fibers. The process includes providing a container containing a liquid preparation, introducing keratinous fibers into the container, and applying at least one impulse to the container to determine the degree of damage. The liquid preparation contains at least two immiscible continuous liquid phases, where the phases differ in densities at 20° C. by at least 0.04 g/ml.

15 Claims, No Drawings

PROCESS FOR DETERMINING THE DEGENERATION LEVEL OF KERATINIC FIBERS

CROSS-REFERENCE TO RELATED APPLICATIONS

This application is a continuation under 35 U.S.C. §365 (c) and 35 U.S.C. §120 of international application PCT/EP00/12265, filed on Dec. 6, 2000, the international application not being published in English. This application also claims priority under 35 U.S.C. §119 to DE 199 59 213.6, filed on Dec. 8, 1999.

BACKGROUND OF THE INVENTION

The invention relates to a process for determining damage to keratinous fibers.

Keratinous fibers—whether as useful materials, such as wool, or as part of biological systems, such as human hair—are exposed to a number of environmental influences which can lead to more or less serious damage to the fibers. In the case of human hair, these can include natural influences, such as strong solar radiation. However, there are also artificial influences, such as blow-drying, combing or brushing and bleaching, permanent waving or coloring, which can also damage the hair if practiced too frequently, too intensively or unprofessionally.

Now, it can be of enormous advantage for the success of certain hair treatments if the hairdresser carrying out the treatment knows the extent to which the hair has been damaged. He/she is then able—on the basis of professional knowledge—to adapt the treatment to the particular degree of damage to the hair or, where necessary, to apply a preliminary repair treatment. In addition, in the case of coloring, it can be critical in the interests of evenness to know whether there is uniform hair damage or no damage at all or whether different parts of the hair have been damaged to different extents, for example hardly any damage at the roots but serious damage at the tips.

Unfortunately, determining the degree of damage by known methods is relatively complicated and, in addition, calls for considerable experience and professional knowledge on the part of the person responsible.

Accordingly, there is a need for a simple process that would enable the degree of damage to keratinous fibers to be at least qualitatively or semiquantitatively determined both simply and quickly. This process would enable the professional hairdresser to determine the individual degree of damage to the hair both quickly and simply and, at the same time, reliably immediately before carrying out the treatment. Ideally, however, this process would enable consumers with no relevant knowledge or experience to choose the optimal product for the degree of damage to his/her hair from the ever increasing selection of modern hair care and hair treatment products.

It has now surprisingly been found that information on the degree of damage to keratinous fibers can be obtained in a quick, simple and highly reproducible manner by means of a preparation comprising two immiscible continuous liquid phases differing in density and polarity.

SUMMARY OF THE INVENTION

Accordingly, the present invention relates to a process for determining the degree of damage to keratinous fibers, more particularly human hair, which is characterized in that the fibers are introduced into a container holding a liquid preparation comprising at least two immiscible continuous liquid phases A, B and optionally C, which differ in their densities at 20° C. by at least 0.04 g/ml, and an impulse is applied to the system.

DETAILED DESCRIPTION OF THE INVENTION

Keratinous fibers in the context of the invention are understood to include wool, pelts and feathers, but especially human hair.

The process according to the invention is based on observations made when hair fibers are introduced into a system of two immiscible liquids differing in polarity. Providing certain conditions—described in detail hereinafter—are maintained, undamaged or lightly damaged fibers preferentially collect in the nonpolar phase while seriously damaged fibers preferentially collect in the polar phase.

In one preferred embodiment, the liquid preparation according to the invention comprises two immiscible continuous phases A and B. The liquid phase with the greater polarity is referred to hereinafter as phase A.

In the context of the present invention, the definition of the "polarity" of a phase relates to the dipole moment of the substance(s) forming the phase. Most of phase A, i.e. 90% by weight or more, based on phase A, is preferably formed by substances with a dipole moment of 1.0 debye or more.

In a first preferred embodiment, all of phase A or more than 90% by weight, based on phase A, consists of water. Other suitable components are, preferably, surfactants, dyes and inorganic or organic salts and perfume oils.

Anionic, ampholytic, zwitterionic, nonionic and cationic surfactants may be used as the surfactants.

Anionic surfactants suitable for carrying out the process according to the invention are any known anionic surfactants. Such surfactants are characterized by a water-solubilizing anionic group such as, for example, a carboxylate, sulfate, sulfonate or phosphate group and a lipophilic alkyl group containing about 10 to 22 carbon atoms. In addition, glycol or polyglycol ether groups, ester, ether and amide and hydroxyl groups may be present in the molecule. Examples of suitable anionic surfactants are:

linear fatty acids containing 10 to 22 carbon atoms (soaps), ether carboxylic acids corresponding to the formula R—O(—$CH_2$—$CH_2$O)$_x$—$CH_2$—COOH, in which R is a linear alkyl group containing 10 to 22 carbon atoms and x=0 or 1 to 16, amide ether carboxylates corresponding to the formula [R—NH(—$CH_2$—$CH_2$—O)$_n$—$CH_2$—COO]$_m$Z, in which R is a linear or branched, saturated or unsaturated acyl group containing 2 to 29 carbon atoms, n is an integer of 1 to 10, m has a value of 1 or 2 and Z is a cation from the group of alkali or alkaline earth metals, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid monoesters and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(—$CH_2$—$CH_2$O)$_x$—$SO_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkyl polypropylene glycol ethers according to DE-A 37 23 354, sulfonates of unsaturated fatty acids containing 12 to 24 carbon atoms and 1 to 6 double bonds according to DE-A 39 26 344, esters of tartaric acid and citric acid with alcohols which represent products of the addition of about 2 to 15 molecules of ethylene oxide and/or propylene oxide onto fatty alcohols containing 8 to 22 carbon atoms, coconut monoglyceride sulfates in the form of the sodium, potassium, magnesium and ammonium and mono-, di- and/or trialkanolammonium salts containing 2 or 3 carbon atoms in the alkanol group.

Preferred anionic surfactants are alkyl sulfates, alkyl polyglycol ether sulfates and ether carboxylic acids containing 10 to 18 carbon atoms in the alkyl group and up to 12 glycol ether groups in the molecule and sulfosuccinic acid monoalkyl and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups.

Nonionic surfactants contain, for example, a polyol group, a polyalkylene glycol ether group or a combination of polyol and polyglycol ether groups as their hydrophilic group. Corresponding compounds are, for example, products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of adducts of 1 to 30 moles of ethylene oxide with glycerol, $C_{8-22}$ alkyl mono- and oligoglycosides and ethoxylated analogs thereof and products of the addition of 5 to 60 moles of ethylene oxide onto castor oil and hydrogenated castor oil.

Preferred nonionic surfactants are alkyl polyglycosides corresponding to the general formula RO(S)$_x$. These compounds are characterized by the following parameters:

The alkyl group R contains 6 to 22 carbon atoms and may be both linear and branched. Primary linear and 2-methyl-branched aliphatic groups are preferred. Corresponding alkyl groups R are, for example, 1-octyl, 1-decyl, 1-lauryl, 1-myristyl, 1-cetyl and 1-stearyl groups. 1-Octyl, 1-decyl, 1-lauryl and 1-myristyl groups are particularly preferred. Where so-called "oxoalcohols" are used as starting materials, compounds containing an odd number of carbon atoms in the alkyl chain predominate.

The alkyl polyglycosides usable in accordance with the invention may contain, for example, only one particular alkyl group R. However, these compounds are normally prepared from natural fats and oils or mineral oils. In this case, the alkyl groups R are mixtures corresponding to the starting compounds or to the particular working-up of those compounds.

Particularly preferred alkyl polyglycosides are those in which R stands essentially for $C_8$ and $C_{10}$ alkyl groups, essentially for $C_{12}$ and $C_{14}$ alkyl groups, essentially for $C_8$ to $C_{16}$ alkyl groups or essentially for $C_{12}$ to $C_{16}$ alkyl groups.

Any monosaccharides or oligosaccharides may be used as the sugar unit S. Sugars containing 5 or 6 carbon atoms and the corresponding oligosaccharides are normally used. Such sugars are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides suitable for use in accordance with the invention contain on average 1.1 to 5 sugar units. Alkyl polyglycosides where x has a value of 1.1 to 1.6 are preferred. Alkyl polyglycosides where x has a value of 1.1 to 1.4 are most particularly preferred.

The alkoxylated homologs of the alkyl polyglycosides mentioned may also be used in accordance with the invention. These homologs may contain on average up to 10 ethylene oxide and/or propylene oxide units per alkyl glycoside unit.

The compounds containing alkyl groups used as surfactants may be pure substances. However, it is generally preferred to produce these compounds from native vegetable or animal raw materials so that mixtures with different alkyl chain lengths, depending on the particular raw material, are obtained.

The surfactants which are adducts of ethylene oxide and/or propylene oxide with fatty alcohols or derivatives of these adducts may be both products with a "normal" homolog distribution and products with a narrow homolog distribution. Products with a "normal" homolog distribution are understood to be mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. It can be of advantage to use so-called narrow-range products.

Zwitterionic surfactants may also be used. Zwitterionic surfactants are surface-active compounds which contain at least one quaternary ammonium group and at least one —COO$^{(-)}$ or —SO$_3$$^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the INCI name of Cocamidopropyl Betaine.

Ampholytic surfactants are also suitable. Ampholytic surfactants are surface-active compounds which, in addition to a $C_{8-18}$ alkyl or acyl group, contain at least one free amino group and at least one —COOH or —SO$_3$H group in the molecule and which are capable of forming inner salts.

Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Examples of cationic surfactants suitable for use in the hair treatment formulations according to the invention are, in particular, quaternary ammonium compounds. Preferred quaternary ammonium compounds are ammonium halides, more particularly chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the readily biodegradable quaternary ester compounds such as, for example, the dialkyl ammonium methosulfates and methyl hydroxyalkyl dialkoyloxyalkyl ammonium methosulfates marketed under the trade name of Stepantex® and the corresponding products of the Dehyquart® series. Other cationic surfactants suitable for use in accordance with the invention are the quaternized protein hydrolyzates.

The inorganic salts present in phase A may be, for example, the halides, more particularly the chlorides, sulfates, phosphates and carbonates of alkali metals, more particularly sodium and potassium, alkaline earth metals, more particularly magnesium, manganese, zinc, iron, copper and aluminium. The organic salts may be selected in particular from the acetates, tartrates and citrates of the above-mentioned metals and the corresponding ammonium and alkanolammonium salts.

The dyes used are preferably the dyes also used in cosmetic products, for example for coloring shampoos.

Preferred perfume oils are those with a fruity smell, for example apple, pear, strawberry, peach, apricot, pineapple, banana, cherry, kiwi, mango, coconut, almond, grapefruit, maracuja, mandarin and melon.

Most of phase B, i.e. more than 90% by weight, based on phase B, consists of nonpolar substances.

In principle, suitable basic constituents of phase B are any water-insoluble oils and fatty compounds. Water-insoluble substances in the context of the invention are substances with a solubility in water at 20° C. of less than 0.1% by weight. The melting point of the individual oil or fatty components should be below 5° C. However, where several oil and fatty components and optionally solid paraffins and waxes are used, it is generally sufficient if the mixture of oil and fatty components satisfies these requirements.

Corresponding oil components are, for example, hydrocarbons, silicone oils, vegetable oils and fatty acids and fatty acid derivatives. Individually or in admixture, these substances should be liquid at least at temperatures of ca. 5° C. to ca. 30° C.

Linear and branched, saturated and mono- or polyunsaturated hydrocarbons may be used as the hydrocarbons. Preferred hydrocarbons are the commercially available paraffin oils and synthetic hydrocarbons and di-n-alkylethers containing a total of 12 to 36 and more particularly 12 to 24 carbon atoms, such as for example di-n-octylether, di-n-decylether, di-n-nonylether, di-n-undecylether, di-n-dodecylether, n-hexyl-n-octylether, n-octyl-n-decylether, n-decyl-n-undecylether, n-undecyl-n-dodecylether and n-hexyl-n-undecylether and di-tert-butylether, diisopentylether, di-3-ethyldecylether, tert.butyl-n-octylether, isopentyl-n-octylether and 2-methylpentyl-n-octylether. The commercially available compounds 1,3-di-(2-ethylhexyl)-cyclohexane (Cetiol® S) and di-n-octylether (Cetiol® OE) may preferably be used.

Other oil components suitable for use in accordance with the invention are fatty acid and fatty alcohol esters. The monoesters of $C_{3-24}$ alcohols are preferred. Substances belonging to this group are products of the esterification of $C_{6-24}$ fatty acids, such as, for example, caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids, with such alcohols as, for example, isopropyl alcohol, caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or the oxidation of aldehydes from Roelen's oxosynthesis and as monomer fraction in the dimerization of unsaturated fatty alcohols. Isopropyl myristate, isononanoic acid $C_{16-18}$ alkyl ester (Cetiol® SN), stearic acid-2-ethylhexyl ester (Cetiol® 868), cetyl oleate, glycerol tricaprylate, coconut fatty alcohol caprate/caprylate and n-butyl stearate are particularly preferred for the purposes of the invention.

Finally, other oil components suitable for use in accordance with the invention are dicarboxylic acid esters, such as di-n-butyl adipate, di-(2-ethylhexyl)-adipate, di-(2-ethylhexyl)-succinate and diisotridecyl acelate, and diol esters, such as ethylene glycol dioleate, ethylene glycol diisotridecanoate, propylene glycol di-(2-ethylhexanoate), propylene diisostearate, propylene glycol dipelargonate, butanediol diisostearate and neopentyl glycol dicaprylate.

Fatty alcohols containing 8 to 22 carbon atoms may also be used as oil components. The fatty alcohols used may be saturated or unsaturated and linear or branched. Examples of fatty alcohols suitable for use in accordance with the invention are decanol, octanol, octenol, dodecenol, decenol, octadienol, dodecadienol, decadienol, oleyl alcohol, erucyl alcohol, ricinolyl alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol and Guerbet alcohols thereof (this list is purely exemplary and is not intended to limit the invention in any way). However, the fatty alcohols emanate from preferably natural fatty acids, normally being obtained from the esters of the fatty acids by reduction. According to the invention, it is also possible to use the fatty alcohol cuts which are produced by reduction of naturally occurring triglycerides, such as bovine tallow, palm oil, peanut oil, rapeseed oil, cottonseed oil, soybean oil, sunflower oil and linseed oil, or fatty acid esters formed from the transesterification products thereof with corresponding alcohols and which therefore represent a mixture of different fatty alcohols.

Preferred fatty acid derivatives according to the invention are esters, ethers, amides and fatty alcohols.

Silicone oils suitable for use in accordance with the invention are more particularly dialkyl and alkylaryl siloxanes such as, for example, dimethyl polysiloxane and methylphenyl polysiloxane and alkoxylated and quaternized analogs thereof. Examples of such silicones are the products marketed by Dow Corning under the names of DC 190, DC 200, DC 344, DC 345 and DC 1401 and the commercial product Fancorsil® LIM-1.

Preferred vegetable oils are sunflower oil, orange oil, almond oil, wheat germ oil and peach kernel oil.

Besides the nonpolar compounds mentioned, phase B may preferably contain oil-soluble surface-active compounds, dyes and perfume oils.

Examples of preferred two-phase systems are the following systems where preferably more than 90% by weight or more of the individual phases consist of the main component mentioned:

(A): dimineralized water/(B): isododecane (A): dimethicone/(B): isododecane

In a preferred embodiment, at least phase A or phase B contains a dye. In a particularly preferred embodiment, different dyes are used in phases A and B.

It has proved to be of advantage for the process according to the invention if the continuous phases differ in their densities at 20° C. by at least 0.1 and more particularly by at least 0.2 g/ml.

In principle, the process may be carried out in containers of any, advantageously transparent, material. In one advantageous embodiment, however, the entire container or large parts thereof consist(s) of glass. One example of such containers are screw-top glass containers with a plastic closure. Basically, there are no limits to the shape of the container. Thus, for aesthetic reasons for example, the shape of the container may be based on the containers used, for example, in the souvenir field for so-called "snow landscapes".

To carry out the process, the hair samples are placed in the container holding the two phases A and B so that, initially, they lie on the surface of the upper phase.

The hair samples selected are 5 to 1,000 and advantageously about 20 to 100 ca. 0.5 to 1 cm long hair fibers substantially equal in length. It has proved to be of advantage to shampoo and dry the hair before cutting off the samples although this is not absolutely essential.

The dimensions of the container and the quantities of phases A and B are advantageously selected so that ca. 5 to 40 hair fibers per cm$^2$ of interface between phases A and B come under examination. In addition, the phase with the lower density—in most cases phase B—should have a height in the container which is shorter than the length of the hair samples. In the interests of clear visibility of the effect, the height of the phase with the greater density should be about 2 to about 10 times greater than the height of the phase with the lower density.

An air gap may be present above the two liquid phases in the container. However, the dimensions of the container may also be selected so that there is hardly any space left for an air gap after closure.

Before applying the impulse, the container holding the two phases and the hair sample is closed. Two ways of applying the impulse have proved to be particularly suitable:
1. The container is turned upside down for ca. 1 second and then returned to its original position. In other words, it is turned through 360° about a horizontal axis.
2. The container is carefully shaken for ca. 10 to 30 seconds. "Carefully shaken" means that the container is shaken only to the extent that the formation of bubbles is avoided as much as possible.

The more seriously the hair samples are damaged, the faster and more completely they move into the polar phase. Accordingly, in the preferred arrangement (where phase A has a greater density than phase B), damaged hair fibers sink to the bottom of the container. By contrast, undamaged or only lightly damaged hair fibers remain on or in the upper phase.

Although, as described above, liquid preparations comprising two immiscible continuous liquid phases A and B are preferred, liquid preparations comprising three immiscible continuous liquid phases A, B and C can bring advantages in individual cases in terms of quick and accurate interpretation of the results. Examples of such three-phase systems are the following systems where 90% by weight or more of the individual phases consist of the main component indicated:

(A): demineralized water/(B): isododecane/(C): perfluorodecalin (A): demineralised water/(B): isododecane/(C): dimethicone (A): demineralized water/(B): 1,3-bis-(2-ethylhexyl)-cyclohexane/(C): propylene carbonate

EXAMPLES

The following Examples are intended to illustrate the invention:

Example 1

Two samples of ca. 50 hair fibers 0.7 cm in length were cut from a sample of healthy Caucasian human hair.

The first sample was washed with a commercially available shampoo and then dried in air.

The second sample was treated twice at an interval of one week with a commercially available "ultrablonding" preparation, then washed with a commercially available shampoo and dried in air.

The samples were then placed in a commercially available wide-necked screw-top glass container with a volume of 30 ml. The container held as phase A:
  23.0 ml of demineralized water
  3 drops of dye solution Kelate Cu (EDTA copper disodium salt (tri-K))
as phase B
  2.0 ml of isododecane
  1 drop of dye Solvent Blue 35 (a product of Ellis & Everard)

The hairs were carefully placed on the surface of the upper liquid. The container was then closed and carefully shaken for 30 seconds as described above.

In the case of the sample with non-pretreated healthy hair, all the hair fibers remained in the upper phase (phase B).

In the case of the sample with the 2×ultrablonded hair fibers, all the fibers were found on the bottom of the container, i.e. in the lower phase (phase A).

Example 2

Ten of the hair fibers cut off as in Example 1 were subjected ten times to different hair-changing treatments.

The degree of damage was then determined by the test according to the invention as described in Example 1.

The hair samples were then subjected to amino acid analysis by the method described by H. D. Spackman, W. H.

Stein and S. Moore in Anal. Chem. (1958), 1190–1206. This amino acid analysis is an established method of characterizing damage to human hair and wool. The higher the level of cysteic acid, the greater the damage to the hair or the wool.

The results obtained with these two methods of determination are set out in the following Table:

| Pretreatment | Amino acid analysis [mol-% cysteic acid] | Process acc. to the invention [sunken hairs (in the lower phase or on the bottom) in %] |
| --- | --- | --- |
| Untreated | 1.8 | 0 |
| 1× bleached | 2.4 | 27 |
| 1× bleached + 1× "permed" | 3.7 | 49 |
| 2× bleached + 2× "permed" | 7.0 | 62 |

What is claimed is:

1. A process for determining the degree of damage to keratinous fibers comprising:
    (a) providing a container comprising a liquid preparation, wherein the liquid preparation comprises at least two immiscible continuous liquid phases, and wherein the phases differ in densities at 20° C. by at least 0.04 g/ml;
    (b) introducing keratinous fibers into the container; and
    (c) applying at least one impulse to the container to determine the degree of damage to the fibers.

2. The process of claim 1 wherein the liquid preparation comprises two immiscible continuous liquid phases A and B.

3. The process of claim 2, wherein the continuous phase A comprises 90 weight percent or more, based on the total weight of phase A, of substances having a dipole moment of 1.0 debye or more.

4. The process of claim 3 wherein the continuous phase A comprises 90 weight percent or more of water, based on the total weight of phase A.

5. The process of claim 4 wherein the continuous phase A consists essentially of water.

6. The process of claim 2 wherein the continuous phase B comprises more than 90 weight percent, based on the total weight of phase B, of one or more nonpolar compounds.

7. The process of claim 6 wherein the nonpolar compounds are selected from hydrocarbons, silicone oils, vegetable oils, fatty acids or fatty acid derivatives, or combinations thereof.

8. The process of claim 7 wherein the nonpolar compounds comprise one or more fatty acid derivatives selected from esters, ethers, amides or fatty alcohols.

9. The process of claim 2 wherein the continuous phases A and B differ in densities at 20° C. by at least 0.1 g/ml.

10. The process of claim 9 wherein the continuous phases A and B differ in densities at 20° C. by at least 0.2 g/ml.

11. The process of claim 2 wherein at least part of the container is made of glass.

12. The process of claim 2, wherein the phase A comprises 90 weight percent or more, based on the total weight of phase A, of water, wherein the phase B comprises more than 90 weight percent, based on the total weight of phase B, of one or more nonpolar compounds selected from hydrocarbons, silicone oils, vegetable oils, fatty acids or fatty acid derivatives, or combinations thereof, and wherein the phases A and B differ in densities at 20° C. by at least 0.1 g/ml densities.

13. The process of claim 12 wherein the phase A further comprises one or more surfactants, dyes, inorganic salts, organic salts or perfume oils, or combinations thereof.

14. The process of claim 12 wherein the liquid preparation further comprises a phase C selected from the groups consisting of perfluorodecalin, dimethicone and propylene carbonate.

15. The process of claim 1 wherein a first phase comprises more than 90 weight percent dimethicone, based on the total weight of the first phase, and a second phase comprises more than 90 weight percent isododecane, based on the total weight of the second phase.

* * * * *